United States Patent
Hohmann

(10) Patent No.: US 12,121,598 B2
(45) Date of Patent: Oct. 22, 2024

(54) RADIATION-CURABLE COMPOSITION FOR USE IN RAPID-PROTOTYPING OR RAPID-MANUFACTURING METHODS

(71) Applicant: KULZER GMBH, Hanau (DE)

(72) Inventor: Alfred Hohmann, Schmitten (DE)

(73) Assignee: KULZER GMBH, Hanau (DE)

( * ) Notice: Subject to any disclaimer, the term of this patent is extended or adjusted under 35 U.S.C. 154(b) by 750 days.

(21) Appl. No.: 17/277,566

(22) PCT Filed: Sep. 20, 2019

(86) PCT No.: PCT/EP2019/075295
§ 371 (c)(1),
(2) Date: Mar. 18, 2021

(87) PCT Pub. No.: WO2020/058464
PCT Pub. Date: Mar. 26, 2020

(65) Prior Publication Data
US 2021/0353508 A1    Nov. 18, 2021

(30) Foreign Application Priority Data

Sep. 21, 2018  (DE) ................... 10 2018 123 330.2

(51) Int. Cl.
| | |
|---|---|
| *C08L 9/00* | (2006.01) |
| *A61K 6/62* | (2020.01) |
| *A61K 6/77* | (2020.01) |
| *A61K 6/818* | (2020.01) |
| *B33Y 70/00* | (2020.01) |
| *B33Y 80/00* | (2015.01) |
| *B60C 1/00* | (2006.01) |
| *C08L 33/10* | (2006.01) |

(52) U.S. Cl.
CPC .............. *A61K 6/62* (2020.01); *A61K 6/77* (2020.01); *A61K 6/818* (2020.01); *B33Y 70/00* (2014.12); *B33Y 80/00* (2014.12); *C08L 33/10* (2013.01); *C08L 2203/02* (2013.01)

(58) Field of Classification Search
CPC ..................................... C08L 9/00; B60C 1/00
USPC ......................................................... 523/115
See application file for complete search history.

(56) References Cited

U.S. PATENT DOCUMENTS

| | | |
|---|---|---|
| 9,023,916 B2 | 5/2015 | Bloemker et al. |
| 9,326,917 B2 | 5/2016 | Maletz et al. |
| 9,833,388 B2 | 12/2017 | Willner et al. |
| 2012/0082959 A1 | 4/2012 | Bloemker et al. |
| 2012/0093741 A1 | 4/2012 | Maletz et al. |
| 2016/0113846 A1 | 4/2016 | Willner et al. |

FOREIGN PATENT DOCUMENTS

| | | | |
|---|---|---|---|
| DE | 10 2015 220 373 A1 | 4/2016 | |
| EP | 2 374 444 A2 | 10/2011 | |
| EP | 2 436 34 A2 | 4/2012 | |
| JP | 2017014453 A | * | 1/2017 |
| WO | 01/30306 A1 | 5/2001 | |

* cited by examiner

*Primary Examiner* — Deve V Hall
(74) *Attorney, Agent, or Firm* — Norris McLaughlin, P.A.

(57) ABSTRACT

A polymerisable, radiation curable composition comprising
(i) monomers comprising:
(a) at least one acrylic acid ester having an additional carboxy group, acrylic acid ester having at least one additional anhydride group of carboxy groups, and/or derivative of the afore-mentioned acrylic acid esters,
(b) at least one di-functional acrylate having a bivalent alicyclic group and/or at least one di-functional methacrylate having a bivalent alicyclic group, and
(c) optionally, at least one disubstituted 4,4'-di(oxabenzene) dialkyl methane of formula I, and
(ii) at least one further component comprising:
(d) at least one photoinitiator for the UV and/or Vis spectral region or a photoinitiator system.

The composition is suitable for producing dental prosthetic parts, orthopaedic appliances or dental pre-forms, having a) a flexural strength 50 MPa, b) an E-modulus ≥1500 MPa, c) a bending fracture ≥1.1 MPa m$^{1/2}$, and/or d) a fracture work >250 J/m$^2$ DIN EN ISO 20795-2.

13 Claims, No Drawings

RADIATION-CURABLE COMPOSITION FOR USE IN RAPID-PROTOTYPING OR RAPID-MANUFACTURING METHODS

This application is a 371 of PCT/EP2019/075295, filed Sep. 20, 2019, which claims foreign priority benefit under 35 U.S.C. § 119 of the German Patent Application No. 10 2018 123 330.2, filed September 21, 2018, the disclosures of which are incorporated herein by reference.

A subject matter of the invention is a polymerisable, radiation curable, in particular UV- Vis-, UV- or Vis-curable, composition comprising (i) monomers and (ii) at least one further component, the (i) monomers comprising
(a) at least one acrylic acid ester having an additional carboxy group, acrylic acid ester having at least one additional anhydride group of carboxy groups and/or derivative of the afore-mentioned acrylic acid esters,
(b) at least one di-functional acrylate having a bivalent alicyclic group and/or at least one di-functional methacrylate having a bivalent alicyclic group,
(c) optionally, at least one disubstituted 4,4'-di(oxabenzene) dialkyl methane of formula I, and
(ii) the at least one further component comprising
(d) at least one photoinitiator for the UV and/or Vis spectral region or an appropriate photoinitiator system. The composition according to the invention is suitable for producing dental prosthetic parts, orthopaedic appliances or dental pre-forms, being characterised by a) a flexural strength of greater than or equal to 50 MPa and/or b) an E-modulus of greater than or equal to 1500 MPa, and/or c) a bending fracture of greater than or equal to 1.1 MPa $m^{1/2}$ and/or d) a fracture work of greater than or equal to 250 $J/m^2$ (DIN EN ISO 20795-2), the said being producible in a rapid prototyping or in a rapid manufacturing or rapid tooling method.

Digital manufacturing methods are becoming increasingly important in addition to manual manufacturing methods. Dental restorations such as e.g. crowns and bridges are produced in a subtractive manner using CAD-CAM technologies for several years. Since only a small part of the material is used in case of this milling technology and the overwhelming majority is discarded, as well as since the tool may only work on one dental component respectively, it should be possible to achieve significant cost advantages in case of generative methods using simultaneous production of many dental components and no or only little waste.

Generative methods are already known in dental field e.g. in the form of laser sintering from CoCr, Ti or polymers for producing crowns and bridges, implant components or models.

Compositions of acrylates or derivatives of acrylates for producing dental restorations having an appropriate characteristics profile in respect of the mechanical requirements in dental field according to DIN EN ISO 207952 are not obtainable up to now (see Quintessenz Zahntech. 2017-43 (10): page 1325). The mechanical properties of currently available materials are consistently low, since only few manufacturers may show a permission according to MPG class IIa for their printable plastics and resins, and most of the resins may only be printed unfilled currently. Therefore, these materials are not suitable for producing definitive dental restorations. There is thus a need for compositions for producing definitive prosthetic parts, orthopaedic appliances or dental pre-forms.

It was the object of the invention to provide a mixture of monomers that may optionally comprise fillers, having good properties in respect of the bending fracture and the fracture work after curing, in particular by means of radiation-curing methods. Preferably, the polymerised mixture should have values for the bending fracture of greater than or equal to 1.1 MPa $m^{1/2}$ and/or for the fracture work of greater than 250 $J/m^2$ (DIN EN ISO 20795-2). In addition, the composition should have the ability to be used in radiation-curing rapid manufacturing (RM) or rapid prototyping (RP) methods. A further object was to provide a composition containing inorganic fillers and having a high transparency as polymerisable composition or as polymerised composition. Optionally, an additional object of the invention is the indication of a filler not resulting in degradation of the transparency of the polymerised composition, as being known for silicon dioxide. In addition, the filler should preferably additionally have a beneficial effect on the physical and mechanical properties of the polymerised compositions. Moreover, it should be possible to add dyes and/or fibres to the composition without the suitability of the composition for use in said methods being interfered. Furthermore, it was the object to provide a composition having fibers and additives, if applicable, in addition to monomers, fillers, initiators, stabilisers, dyes, from which dental products and dental prosthetic parts may be produced by means of light-curing RM methods or RP methods.

Presently, dental products are in particular understood to mean dental products being producible from polymerisable compositions, such as e.g. not exhaustive total protheses, provisional crowns and bridges, inlays, onlays, total crowns, occlusal splints, surgical guides for implantology, splints for orthodontic corrections (similar to Invisalign), mouthguards, artificial teeth.

A subject matter of the invention is a composition comprising monomers and optionally pre-polymers (oligomers) and/or polymers comprising at least one acrylic acid ester having an additional carboxy group, acrylic acid ester having at least one additional anhydride group of carboxy groups and/or derivative of the afore-mentioned acrylic acid esters as well as optionally at least one inorganic filler. The radiation-cured composition has a high transparency, preferably of at least 95%, in particular greater than 97%, preferably of 98% (measured at colour test specimen of 1 mm thickness, produced in metal moulds, by means of colorimeter SF 600 (Datacolor)).

In order to meet high aesthetic requirements, compositions usable in dental field for producing definitive dental restorations, such as e.g. work models, orthodontic models, surgical guides, temporary protheses and splints, must have a high degree of transparency. This transparency is usually achieved by optimal adaption of the refractive indices of the fillers and the polymer matrix. However, due to various physical and chemical boundary conditions, very narrow limits are set for the selection of both fillers and monomers.

Thus, typical dental glass fillers have refractive indices in the range of 1.50 to 1.54. Likewise, many suitable monomers for dental materials also have a refractive index in this range. However, the composition demixes due to significantly higher density of the dental glasses, so that rheology modifiers such as e.g. pyrogenic silicas ("aerosils") are added normally. Pyrogenic silicas, in turn, have a refractive index of 1.46 being unfavourable for the desired transparency and being widely outside the optimal range of desired refractive indexes (>1.50) for polymerisable compositions. Therefore, the transparency of the polymeric material produced thereof deteriorates with addition of said rheology modifiers.

This problem may be solved using a zirconium-doted silicon dioxide filler, in particular using a mixed oxide of zirconium dioxide and silicon dioxide. Particularly preferred are i.a. agglomerated mixed oxides, comprising 75 to 99% by weight silicon dioxide and from 1 to 25% by weight zirconium dioxide, based on the total composition of the mixed oxide, in particular the mixed oxide comprises from 85 to 90% by weight silicon dioxide and 10 to 15% by weight zirconium dioxide, wherein it is further preferred for the primary particles of the agglomerated oxide particles to comprise microcrystalline domains of 4 to 7 nm and for the crystallinity index to be advantageously 0.6 to 0.7—determined according to the method of Windisch et al. (WO 01/30306A)—and for the agglomerated oxide particles to be surface-modified with an organofunctional silane being reactive with respect to at least one monomer and/or polymer component. Said agglomerated oxide particles treated according to the invention have outstanding properties in abrasion measurements, regarding the gloss level, an outstanding transparency and very good values in reflexion and roughness measurements after a toothbrush test.

It is also important for the selection of monomers that they interconnect well with the filler optionally used. Normally, polyurethanes, acrylates, polyesters and other monomers do not take a good bond with the fillers used. Therefore, the fillers are normally silanised or hydrophobized at the surfaces to improve bonding with the monomers.

It has surprisingly been found that also acidic monomers attach well to the filler particles. According to the invention, a composition is provided having a polymerisable monomer having a free carboxy group and/or anhydride group, wherein the composition additionally has a di-functional acrylate or methacrylate having an alicyclic group and at least one photoinitiator.

If no inorganic fillers may be used in the polymerisable composition due to the specific dental application, e.g. due to the viscosity aimed of the composition, there is the possibility to use dyes or pigments in the composition for reflection of the irradiation, in particular diffuse reflection or scattering respectively of the incoming irradiation. Dyes are considered as compounds being soluble in the polymerisable composition and form a clear solution preferably.

The radiation-curable compositions according to the invention may preferably be irradiated using a radiation source emitting light in the Vis spectral region, particularly preferred are radiation sources emitting irradiation from 360 to 750 nm, in particular at approx. 385 nm, particularly preferably at approx. 405 nm. Particularly preferably, the composition according to the invention may be irradiated using a polychromatic radiation source, such as a DLP projector, or preferably using a monochromatic radiation source, such as a laser projector, in the Vis spectral region from 380 to 660 nm.

The content of photoinitiator may be reduced in the composition when these pigments and/or dyes being added. A content of photoinitiator being too high may result in a so-called "overcuring" of the irradiated composition, an embrittlement, so that the dental parts produced appropriately are not usable.

Use of the inorganic fillers, pigments or dyes according to the invention leads to even scattering of the radiation source, in particular of the UV and Vis radiation source, in the monomer matrix of the composition, so that an even curing of the composition is anticipated. Ultimately, the polymerised compositions have higher values of fracture work achieved.

The composition according to the invention has the following properties a) flexural strength of greater than or equal to 50 MPa, in particular greater than or equal to 75 MPa and/or b) an E-modulus of greater than or equal to 1500 MPa, in particular greater than or equal to 2000 MPa, and/or c) a bending fracture of greater than or equal to 1.1 MPa $m^{1/2}$, greater than or equal to 1.7 MPa $m^{1/2}$ and/or d) a fracture work of greater than 250 $J/m^2$, in particular greater than or equal to 270 $J/m^2$, each determined according to DIN EN ISO 20795-2 after irradiation using a radiation source in the Vis spectral region, in particular from 385 to 405 nm, preferably after irradiation in a stereolithography method and obtaining a polymerised composition preferably in the form of a blank, dental prosthetic part, orthopaedic appliance or dental pre-form, as well as optional tempering of the polymerised composition using a radiation source.

Post-curing or post-tempering respectively may preferably be carried out e.g. using a laboratory light device (HiLite Power 3D) or in the light furnace preferably using a light spectrum of 390-540 nm.

A subject matter of the invention is a polymerisable, radiation-curable composition, in particular polymerisable by means of UV-Vis, UV or Vis radiation, comprising (i) monomers, preferably a mixture of monomers, and (ii) at least one further component, the (i) monomers comprising
(a) at least one acrylic acid ester having an additional carboxy group, acrylic acid ester having at least one additional anhydride group of carboxy groups and/or derivative of the afore-mentioned acrylic acid esters,
(b) at least one di-function acrylate having a bivalent alicyclic group and/or at least one di-functional methacrylate having a bivalent alicyclic group, preferably being selected from tricyclodecane dimethanol diacrylate (TCDDA), tricyclodecane dimethanol dimethacrylate (TCDA), tricyclodecane diethanol diacrylate, tricyclodecane diethanol dimethacrylate and/or mixture thereof,
(c) optionally, at least one disubstituted 4,4'-di(oxabenzene) dialkyl methane of formula I

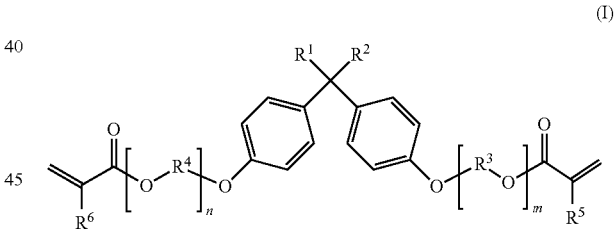

(I)

with $R^1$, $R^2$, $R^5$ and $R^6$ each independently selected from H or C1 to C4 alkyl, in particular with $R^1$ and $R^2$ equal to C1 to C4 alkyl, preferably methyl, and with $R^5$ and $R^6$ the same and selected from H, methyl or ethyl, in particular with $R^5$ and $R^6$ the same and selected from H or methyl, and with $R^3$ and $R^4$ each bivalent C1 to C4 alkylene, with n=0 to 6 and m=0 to 6, and (ii) the at least one further component
(d) comprises at least one photoinitiator for the UV and/or Vis spectral region or a photoinitiator system.

In a preferred alternative, $R^1$ and $R^2$ in formula I may be methyl each, and $R^5$ and $R^6$ may be the same and selected from H, methyl and ethyl, preferably $R^5$ and $R^6$ are the same and selected from H and methyl, and with $R^3$ and $R^4$ each independently bivalent ethylene or propylene with n=1 to 6, preferably being n=2 to 4, and with m=1 to 6, particularly preferably n=2 to 4 and m=2 to 4, more preferably with n=2 and m=2 or with n=4 and m=4 as well as mixtures thereof. Particularly preferred is a mixture of 4,4'-di(oxabenzene) dialkyl methane of formula I a) with $R^1$ and $R^2$ each methyl, and $R^5$ and $R^6$ equal to H and with $R^3$ and $R^4$ each independently bivalent ethylene with n=1 to 6, preferably n=2 to 4, and with m=1 to 6, preferably m=2 to 4, preferably n=4 and m=4 as well as mixtures thereof in mixtures with b) with $R^1$ and $R^2$ each methyl, and $R^5$ and $R^6$ equal to methyl and with $R^3$ and $R^4$ each independently bivalent ethylene with n=1 to 6, preferably n=2 to 4, and with m=1 to 6, preferably m=2 to 4, preferably with n=2 and m=2 as well as mixtures thereof.

Optionally, the composition may additionally comprise at least one polyether diacrylate, such as poly(ethylene glycol) diacrylate, poly(ethylene glycol) di(alkyl) acrylate, poly(propylene glycol) diacrylate, poly(propylene glycol) di(alkyl) acrylate, or a mixture containing at least two of the said monomers. Preferred polyether diacrylates may be selected from triethylene glycol dimethacrylate, diethylene glycol dimethacrylate and/or tetraethylene glycol dimethacrylate. Alternatively or additionally, the composition may comprise diacrylates selected from decanediol di(meth)acrylate, dodecanediol di(meth)acrylate, hexyldecanediol di(meth)acrylate, butanediol di(meth)acrylate or mixtures containing at least one of the acrylates.

The indication in parentheses in the terms (methyl)acrylate or (alkyl)acrylate means that the acrylates may be present as acrylate or methyl acrylate as well as alternatively as alkyl acrylate.

Furthermore, it is preferred for the composition to contain as (a) the at least one acrylic acid ester having an additional carboxy group, acrylic acid ester having at least one additional anhydride group of carboxy groups and/or at least one derivative of the afore-mentioned acrylic acid esters, in particular (alkyl)acrylic acid ester with alkyl C1 to C4 alkyl groups, preferably with alkyl equal to methyl or ethyl, selected from an acrylic acid ester having an additional carboxy group of formula II or III,

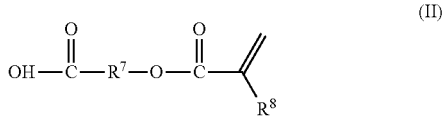

(II)

with $R^7$ each independently selected from bivalent C, H, O and optionally N containing groups with 1 to 50 C atoms, in particular with 1 to 25 C atoms, preferably 8 to 25 C atoms, in particular bivalent aromatic esters, aromatic urethanes, alkylene esters, alkyl urethanes, aromatic ethers, alkyl ethers, and $R^8$ selected from H and 1 to 4 C alkyl, preferably $R^7$ is a bivalent aromatic ester, preferably an ester of a phthalate and $R^8$ is H, methyl or ethyl,

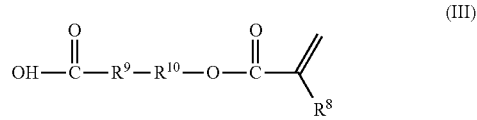

(III)

wherein $R^9$ may be independently selected from bivalent benzoyl, salicyloyl and derivatives thereof or —C—, $R^{10}$ may be a bivalent —$(OR^{11})$—, with $R^{11}$ equal to ethylene or propylene and with r=0 to 10, in particular with r=1 to 6, preferably r=1, particularly preferably —$(OR^{11})$— may be a bivalent group derived from poly(alkylene glycol), in particular poly(propylene glycol) or poly(ethylene glycol) with 1 to 6 propylene glycol or ethylene glycol units sein, or $R^{10}$ may be independently selected from bivalent alkylene and $R^8$ may be selected from H and 1 to 4 C alkyl, preferably $R^8$ is H, methyl or ethyl.

Another subject matter of the invention is a composition that may comprise as (a) at least one acrylic acid ester having an additional carboxy group, acrylic acid ester having at least one additional anhydride group of carboxy groups and/or derivative of the afore-mentioned acrylic acid esters, in particular 2-acryloyloxy ethyl hydrogen phthalate, polyether-functionalised acrylic acid esters having a carboxy group, preferably the composition comprises polyether-functionalised acrylic acid esters having a carboxy group at acryl, polyether-functionalised acrylic acid ester having a carboxy group at alkyl, in particular the polyether being based on poly(propylene glycol) and poly(ethylene glycol) with 1 to 6 glycol units, and/or 4-(2-methacryloxyethyl) trimellitic acid anhydride (4-META, 2-[(2-methyl-1-oxoallyl)oxy]ethyl-1,3-dihydro-1, 3-dioxoisobenzofurane-5-carboxylate).

According to the invention, the composition comprises 2-acryloyloxyethyl hydrogen phthalate optionally in mixture with 2-hydroxyethyl acrylate, 2-hydroxyethyl methacrylate or hydroxypropyl (meth)acrylate.

Likewise preferred monomers as at least one further monomer in the composition may be selected from:
(e.1) at least one mono-, tri-, tetra- or multi-functional monomer, in particular not being a urethane (meth)acrylate, and/or
(e.2) at least one at least di-functional urethane (meth)acrylate.

Preferably, hydroxyethyl acrylate is used as mono-functional monomer. Likewise, hydroxypropyl acrylate, hydroxyethyl methacrylate, hydroxypropyl methacrylate and/or hydroxyethyl acrylate optionally as mixture of at least two of the afore-mentioned monomers may be used.

According to an alternative, preferred are compositions comprising inorganic fillers as further component that are selected from (f) inorganic fillers, inorganic oxides or inorganic mixed oxides, in particular oxides of zirconium and/or silicon and/or dental glasses, preferred is zirconium dioxide or mixed oxide of zirconium oxide or zirconium dioxide and silicon dioxide, silicon dioxide, particularly preferred fillers are mixed oxides of zirconium dioxide and silicon dioxide. Particularly preferred are mixed oxides of zirconium dioxide and silicon dioxide having primary particle sizes in the range of less than 100 nm, optionally being present as agglomerated with 2 to 5 μm. Preferably, the said oxides or mixed oxides are substantially x-ray amorphous. Aluminosilicate glasses, fluoroaluminosilicate glasses and/or barium aluminium silicate may be used as dental glasses. The oxides may be selected from the afore-mentioned as well as from amorphous spherical fillers on the basis of oxide or mixed oxide.

The particle sizes of the inorganic fillers, such as of the at least one inorganic oxide, mixed oxide or dental glass, e.g. comprising barium aluminium oxide, have an average particle diameter of $d_{50}$ less than 10 μm for the present application, particularly preferably the fillers have a particle diameter of approximately 3 to 70 nm, in particular of 10 to 50 nm (nanometers), optionally the particles may be aggregated or agglomerated as particles with up to 10 μm. The primary particles sizes of the inorganic fillers, which may optionally be present as agglomerated and/or aggregated primary particles, have an average particle diameter of approximately 3 to 70 nm, in particular of 10 to 50 nm. Preferably, the mixed oxides of zirconium dioxide with silicon dioxide have a primary particle size of 3 to 70 nm.

The advantage of the very small particle diameters, which may be aggregated and/or agglomerated as appropriate, is that the light is scattered in a substantially diffuse manner by these particles in case of radiation curing and thus leads to better curing in stereolithography methods or DLP methods.

A specific composition according to the invention may comprise:
(a) 1 to 60% by weight of at least one acrylic acid ester having an additional carboxy group, of an acrylic acid ester having at least one additional anhydride of carboxy groups and/or of derivatives of the afore-mentioned acrylic acid esters,
(b) 1 to 30% by weight of at least one di-functional acrylate having a bivalent alicyclic group and/or of at least one di-functional methacrylate having a bivalent alicyclic group,
(c) 0 to 50% by weight optionally of at least one disubstituted 4,4'-di(oxabenzene) dialkyl methane of formula I with $R^1$, $R^2$, $R^5$ and $R^6$ each independently selected from H or C1 to C4 alkyl, in particular $R^1$ and $R^2$ C1 to C4 alkyl, preferably methyl, and $R^5$ and $R^6$ the same and selected from H, methyl or ethyl, in particular $R^5$ and $R^6$ the same and selected from H or methyl, and with $R^3$ and $R^4$ each bivalent C1 to C4 alkylene, with n=0 to 6 and m=0 to 6,
(d) 0.01 to 10% by weight photoinitiator for the UV and/or Vis spectral region,
(e.1) 0 to 25% by weight of at least one mono-, tri-, tetra- or multi-functional monomer, in particular not being a urethane (meth)acrylate, and/or
(e.2) 0 to 25% by weight of at least one at least di-functional urethane (meth)acrylate, and
(f) 0 to 10% by weight, in particular 0.01 to 7.5% by weight, inorganic fillers comprising inorganic oxides or inorganic mixed oxides and/or dental glasses, in particular zirconium dioxide, mixed oxides of zirconium oxide and silicon dioxide, silicon dioxide, the total composition amounting to 100% by weight.

A further specific composition according to the invention may comprise:
(a) 10 to 50% by weight, in particular 20 to 55% by weight, of at least one acrylic acid ester having an additional carboxy group, of an acrylic acid ester having at least one additional anhydride of carboxy groups and/or of derivatives of the afore-mentioned acrylic acid esters,
(b) 5 to 25% by weight of at least one di-functional acrylate having a bivalent alicyclic group and/or of at least one di-functional methacrylate having a bivalent alicyclic group,
(c) 1 to 50% by weight, in particular 15 to 50% by weight, of at least one disubstituted 4,4'-di(oxabenzene) dialkyl methane of formula I with $R^1$, $R^2$, $R^5$ and $R^6$ each independently selected from H or C1 to C4 alkyl, in particular $R^1$ and $R^2$ C1 to C4 alkyl, preferably methyl, and $R^5$ and $R^6$ the same and selected from H, methyl or ethyl, in particular $R^5$ and $R^6$ the same and selected from H or methyl, and with $R^3$ and $R^4$ each bivalent C1 to C4 alkylene, with n=0 to 6 and m=0 to 6,
(d) 0.01 to 10% by weight photoinitiator for the UV and/or Vis spectral region,
(e.1) 0.01 to 15% by weight of at least one mono-, tri-, tetra- or multi-functional monomer, in particular not being a urethane (meth)acrylate, and/or
(e.2) optionally 10 to 20% by weight of at least one at least di-functional urethane (meth)acrylate, and
(f) optionally 0.01 to 7.5% by weight inorganic fillers comprising inorganic oxides or inorganic mixed oxides and/or dental glasses, in particular zirconium dioxide, mixed oxides of zirconium oxide and silicon dioxide, silicon dioxide, the total composition amounting to 100% by weight.

A further particularly preferred composition according to the invention may comprise:
(a) 30 to 55% by weight of at least one acrylic acid ester having an additional carboxy group, of an acrylic acid ester having at least one additional anhydride of carboxy groups and/or of derivatives of the afore-mentioned acrylic acid esters,
(b) 15 to 25% by weight of at least one di-functional acrylate having a bivalent alicyclic group and/or of at least one di-functional methacrylate having a bivalent alicyclic group,
(c) 20 to 50% by weight of at least one disubstituted 4,4'-di(oxabenzene) dialkyl methane of formula I with $R^1$, $R^2$, $R^5$ and $R^6$ each independently selected from H or C1 to C4 alkyl, in particular $R^1$ and $R^2$ 01 to C4 alkyl, preferably methyl, and $R^5$ and $R^6$ the same and selected from H, methyl or ethyl, in particular $R^5$ and $R^6$ the same and selected from H or methyl, and with $R^3$ and $R^4$ each bivalent C1 to C4 alkylene, with n=0 to 6 and m=0 to 6,
(d) 0.01 to 10% by weight photoinitiator for the UV and/or Vis spectral region,
(e.1) 0.5 to 10% by weight of at least one mono-, tri-, tetra- or multi-functional monomer, in particular not being a urethane (meth)acrylate, and/or
(f) optionally 0.01 to 7.5% by weight inorganic fillers comprising inorganic oxides or inorganic mixed oxides and/or dental glasses, in particular zirconium dioxide, mixed oxides of zirconium oxide and silicon dioxide, silicon dioxide, the total composition amounting to 100% by weight.

Furthermore, it is preferred for the composition not to be thixotropic. In addition, it is particularly preferred for the composition to have a viscosity of less than 5000 m·Pas, in particular of 500 to less than 4000 m·Pas, preferably of 500 to 3000 m·Pas, particularly preferably of 500 to 1500 m·Pas. The viscosity is preferably measured according to DIN 1342-2;2003-11 Newtonian liquids or DIN 1342-3;2003-11 non-Newtonian liquids with a rheometer (Anton Par, Physica MCR 301, viscosity range 200-5000 m·Pas at 100/s 23° C.). The compositions according to the invention have no or preferably only a low thixotropy. The compositions produced are structurally viscous, wherein it is preferred for the compositions to be structurally viscous with and without fillers. According to another embodiment, it is preferred for the said to have almost no changes in viscosity over a longer storage period. Furthermore, the compositions have a very good reactivity when being irradiated using a laser or DLP projector.

Work pieces or three-dimensional form bodies may be printed having very good geometrical precision/resolution using the compositions according to the invention. Furthermore, the work pieces show good colour stability.

A subject matter of the invention is a polymerised composition, preferably as dental prosthetic part, orthopaedic appliance or dental pre-from, obtainable by irradiating a polymerisable composition.

Preferably, the polymerised, in particular radiation-cured, composition, preferably as dental prosthetic part, orthopaedic appliance or dental pre-form cumulatively has the following properties: a) a flexural strength of greater than or equal to 50 Mpa, in particular greater than or equal to 70 MPa, and b) an E-modulus of greater than or equal to 1500 Mpa, in particular greater than or equal to 2000 MPa, and/or c) a bending fracture of greater than or equal to 1.1 MPa m$^{1/2}$, in particular greater than or equal to 1.8 MPa m$^{1/2}$, and d) a fracture work of greater than 250 J/m$^2$, in particular greater than 270 J/m$^2$, the properties having been determined according to DIN EN ISO 20795-2. Polymerised compositions without inorganic fillers may have a fracture work of greater than 390 J/m$^2$.

According to a further alternative embodiment, polymerised compositions are obtainable, in particular radiation-cured compositions, in particular UV-Vis-cured compositions, preferably being radiation-cured from all sides additionally, which alternatively or cumulatively have the following properties: a) a flexural strength of greater than or equal to 75 MPa, and/or b) an E-modulus of greater than or equal to 2000 MPa, and/or c) a bending fracture of greater than or equal to 1.7 MPa m$^{1/2}$ and/or d) a fracture work of greater than 250 J/m$^2$, each being determined according to DIN EN ISO 20795-2.

An additional radiation-curing from all sides is understood to mean post-tempering in a 3D light furnace for example.

Preferably, the polymerised compositions have a ratio of E-modulus/flexural strength of less than 26, preferably less than 24, and in particular in combination with a fracture work of greater than 250 J/m$^2$, preferably greater than or equal to 280 J/m$^2$, each determined according to DIN EN ISO 20795-2.

Another subject matter of the invention is a blank in the form of a three-dimensional form body of a polymerised composition, preferably being radiation-cured from all sides additionally, which is suitable for producing prosthetic parts, orthopaedic appliances or dental pre-forms, the blank having a) a flexural strength of greater than or equal to 75 MPa, and/or b) an E-modulus of greater than or equal to 2000 MPa, and/or c) bending fracture of greater than or equal to 1.7 MPa m$^{1/2}$, and/or d) a fracture work of greater than 250 J/m$^2$, each determined according to DIN EN ISO 20795-2. The blank may preferably be present in the form of an artificial tooth which must merely be polished for final individual adjustment to the patient, or requires slight post-processing of the occlusal plane respectively.

Furthermore, a subject matter of the invention is the use of a composition for producing dental prosthetic parts, orthopaedic appliances or dental pre-forms in a rapid prototyping or in a rapid manufacturing, i.e. the production of dental prosthetic parts, or rapid tooling method.

In this context, the following methods—rapid prototyping or rapid manufacturing, a method for producing work pieces, such as a dental prosthetic part, or rapid tooling, a method for producing tools—each comprise stereolithography methods and DLP methods. Optionally, post-tempering with UV, Vis or UV-Vis light may be carried out in the afore-mentioned methods after curing of the polymerisable composition. Preferably, post-tempering of the polymerised composition or of the dental prosthetic parts, of the orthopaedic appliances or dental pre-forms or blanks is carried out concurrently from at least three sides, preferably from five to six sides, as it is possible in a light furnace. Alternatively, the polymerised composition may be tempered alternatively or additionally.

The dental prosthetic parts comprise a denture base or parts thereof, e.g. as replication of a gingiva or a part thereof, artificial teeth, dental arch having at least two to 16 artificial teeth being interdentally integrally connected, crowns, provisional crowns, total prostheses, total crowns, splints for orthodontic corrections (similar to Invisalign), dental bridges, abutments, suprastructures, dental bars, inlays, onlays, orthodontic appliances, such as occlusal splints, dental pre-forms of artificial teeth, surgical guides for implantology, mouthguards, and/or implants.

Colour pigments may additionally be added to the composition to adjust the colour. In addition, red fibres may be added to the composition to imitate blood vessels of the gingiva. Suitable colour pigments are for example: PV pigment red—CAS 4948-15-6, pigment blue 220943—CAS 68186-87-8, pigment black 100—CAS 68186-91-4, kronos 2220—CAS 13463-67-7 and light yellow 3R—CAS 68186-90-3. Layer thickness in the range of 5 µm to 250 µm per curing layer may be achieved in the polymerised compositions.

High transparency may be achieved by optimal selection of the recipe components in respect of their refractive indices.

In an alternative, the mono-functional monomer may contain at least one of the said monomers: methyl methacrylate as well as optionally additionally ethyl methacrylate, propyl methacrylate, butyl methacrylate, n-hexyl methacrylate, 2-phenoxyethyl methacrylate, isobornyl methacrylate, isodecyl methacrylate, polypropylene glycol monomethacrylate, tetrahydrofuryl methacrylate, methyl acrylate, ethyl acrylate, propyl acrylate, butyl acrylate, n-hexyl acrylate, 2-phenoxyethyl acrylate, isobornyl acrylate, isodecyl acrylate, polypropylene glycol monoacrylate, tetrahydrofuryl acrylate, benzyl, furfuryl or phenyl (meth) acrylate, a mixture containing at least one of said (meth) acrylates and/or co-polymers comprising one or at least two of the afore-mentioned monomers.

A preferred composition is structurally viscous, i.e. the composition preferably changes its viscosity under shear stress.

Furthermore, the composition may comprise monomers which are selected from tri-, tetra- or multi-functional monomer, not being a urethane (meth)acrylate, pentaerythritol tetraacrylate, trimethylol propane tri(meth)acrylate and/or pentaerythritol tetra(meth)acrylate.

Benzoin alkyl ethers or esters, benzil monoketales, acylphosphine oxides or aliphatic and aromatic 1,2-diketo compounds, such as for example 2,2-diethoxyacetophenone, 9,10-phenanthrene quinone, diacetyl, furil, anisil, 4,4'-dichlorobenzil and 4,4'-dialkoxybenzil or camphorquinone, are conceivable as photoinitiators for example. The photoinitiators are preferably used together with a reducing agent. Examples for reducing agents include amines such as aliphatic or aromatic tertiary amines, for example N,N-dimethyl-p-toluidine or triethanol amine, cyan ethyl methyl aniline, triethyl amine, N,N-dimethyl aniline, N-methyl diphenyl amine, N,N-dimethyl-sym.-xylidine, N,N-3,5-tetramethyl aniline and 4-dimethyl aminobenzoic acid ethyl ester or organic phosphites. Usual photoinitiator system are e.g. camphor quinone plus ethyl-4-(N,N-dimethylamino) benzoate, 2-(ethylhexyl)-4-(N,N-dimethylamino)benzoate or N,N-dimethyl aminoethyl methacrylate.

2,4,6-trimethylbenzoyl diphenyl phosphine oxide is particularly suitable as initiator for the polymerisation initiated by UV light. UV photoinitiators may be used alone or in combination with an initiator for visible light.

Particularly preferred photoinitiators and/or initiator systems comprise a) at least one radical photoinitiator, in particular at least one peroxide and/or azo compound, in particular LPO: dilauroyl peroxide, BPO: dibenzoyl peroxide, t-BPEH: tert-butylper-2-ethylhexanoate, AIBN: 2,2'-azobis-(isobutyronitrile), DTBP: di-tert-butylperoxide, or an alpha-hydroxyketone, camphorquinone, acylphosphine oxide. Optionally, stabilisers may be added in addition, and optionally b) at least one co-initiator such as an amine, normally a tert-amine, in particular at least one aromatic amine, such as N,N-dimethyl-p-toluidine, N,N-dihydroxyethyl-p-toluidine and/or p-dibenzyl aminobenzoic acid diethylester.

Typical stabilisers comprise 2,6-di-tert.-butyl-4-methylphenol (BHT) or hydroquinone monomethyl ether (MEHQ).

The invention is explained in more detail by the following examples without limiting the invention to these exemplary embodiments.

Post-curing/Post-tempering was carried out i.a. using a laboratory light device HiLite Power 3D.

TABLE 1a

Compositions according to the invention

| Raw material | Example 1 orig. sample weight in g | Example 2 orig. sample weight in g |
|---|---|---|
| UV09 | 0.31 | 0.31 |
| Irgacure 819 | 1 | 1 |
| ethoxylated (2)bisphenol A diacrylate | 20 | 30 |
| ethoxylated (4)bisphenol A diacrylate | 6.25 | 6.25 |
| carboxy acrylate | 47.03 | 37.29 |
| 2-hydroxyethyl acrylate | 1.22 | 0.96 |
| tricyclodecane dimethanol diacrylate (TCDDA) | | 10 |
| (octahydro-4,7-metano-1H indenyl) methyl acrylate - TCDA | 19.86 | 9.86 |
| Makrolexorange | | 0.004 |
| zirkonium (20-25% by wt.) silica (75-80 Gew.-%) mixed oxide | 5 | |
| tot. | 100.67 | 95.68 |
| = | 100% by wt. | 100% by wt. |

EXEMPLARY EMBODIMENTS

The mixture produced was used to print test specimens for the following tests on a 3D precision printer having the wavelength 405 nm (Cara Print 4.0). The test specimens were washed up with isopropanol after the printing process and subjected to a tempering process. The said was carried out by lighting on both sides in a laboratory light device HiLite Power 3D, 200 W (Kulzer GmbH) for 5 min respectively or as specified by the manufacturer.

Properties of the mixture according to the invention for splinting materials, tested according to DIN EN ISO 20795-2.

TABLE 1b

Compositions according to the invention

| | Example 1 with fillers (zirconium silica mixed oxide) | Example 2 with pigments |
|---|---|---|
| cara Print 4.0-50 µm | 50 | 50 |
| HiLite Power 3D - 2 × 5 min | 2 × 5 min | 2 × 5 min |
| flexural strength in MPa | 95.5 | 89.5 |
| E-modulus in MPa | 2508 | 2123 |
| bending fracture in MPa m$^{1/2}$ | 1.88 | 2.04 |
| fracture work in J/m$^2$ | 280.7 | 404.4 |

TABLE 2

Comparative examples with acrylates

| Raw material | Comp. Example 1 orig. sample weight in g | Comp. Example 2 orig. sample weight in g |
|---|---|---|
| UV09 | 0.31 | 0.31 |
| Irgacure 819 | 1 | 1 |
| ethoxylated (2)bisphenol A diacrylate | 30 | 30 |
| ethoxylated (4)bisphenol A diacrylate | 6.25 | 6.25 |
| Tricyclodecane dimethanol diacrylate (TCDDA) | 10 | 10 |
| Genomer 3364 (modified polyether polyol acrylate) | 38.25 | |
| Genomer 4316 (aliphatic polyester urethane acrylate) | | 38.25 |
| (octahydro-4,7-metano-1H indenyl) methyl acrylate - TCDA | 9.86 | 9.86 |
| Makrolexorange | 0.004 | 0.004 |
| zirconium (20-25% by wt.) silica (75-80% by wt.) mixed oxide | | |
| tot. | 95.68 | 95.68 |
| = | 100% by wt. | 100% by wt. |

TABLE 2b

Comparative examples with acrylates

| | Comp. Example 1 | Comp. Example 2 |
|---|---|---|
| cara Print 4.0-50 µm | 50 | 50 |
| HiLite Power 3D - 2 × 5 min | 2 × 5 min | 2 × 5 min |
| flexural strength in MPa | 36.5 | 43.5 |
| E-modulus in MPa | 1932 | 841 |
| bending fracture in MPa m$^{1/2}$ | 0.64 | 1.28 |
| Fracture work in J/m$^2$ | 50.35 | 269.8 |

TABLE 3

Compositions state of the art

| | Competitor 1 Next Dent Dima ortho | Competitor 2 DMG Luxa Print | Competitor 3 Detax (Ortho Free Print |
|---|---|---|---|
| cara Print 4.0 | 50 | 50 | 50 |
| Hilite Power 3D | 2 × 5 min | 2 × 5 min | 2 × 5 min |
| flexural strength in MPa | 71.1 | 44.8 | 60 |
| E-modulus in MPa | 2018 | 1052 | 1443 |
| bending fracture in MPa m$^{1/2}$ | 1.1 | 0.88 | 0.7 |
| fracture work in J/m$^2$ | > 250 | 127 | 131.8 | 58.9 |

The invention claimed is:

1. Polymerisable, radiation-curable composition comprising
   (i) monomers and
   (ii) at least one further component, wherein
   the composition comprises
   (a) 30 to 60% by weight of at least one acrylic acid ester having an additional carboxy group, of an acrylic acid ester having at least one additional anhydride of carboxy groups and/or of derivatives of the afore-mentioned acrylic acid esters,
   (b) 5 to 30% by weight of at least one di-functional acrylate having a bivalent alicyclic group and/or of at least one di-functional methacrylate having a bivalent alicyclic group, (c) 15 to 50% by weight optionally of at least one disubstituted 4,4'-di(oxabenzene) dialkyl methane of formula I

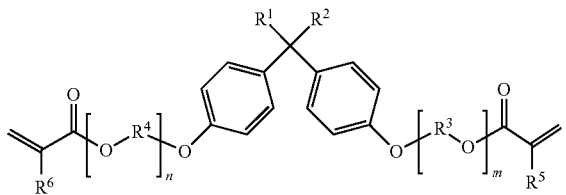

with $R^1$, $R^2$, $R^5$ and $R^6$ each independently selected from H or C1 to C4 alkyl, and with $R^3$ and $R^4$ each bivalent C1 to C4 alkylene with n=1 to 6 and m=1 to 6, (d) 0.01 to 10% by weight photoinitiator for the UV and/or Vis spectral region or a photoinitiator system for the UV and/or Vis spectral region selected from benzoin alkyl ethers or esters, benzil monoketales, acylphosphine oxides or aliphatic and aromatic 1,2-diketo compounds, (e.1) 0.5 to 25% by weight of at least one mono-, tri-, tetra- or multi-functional monomer not being a urethane (meth)acrylate, and/or (e.2) 0 to 25% by weight of at least one at least di-functional urethane (meth)acrylate, (f) optionally 0.01 to 10% by weight inorganic fillers comprising inorganic oxides or inorganic mixed oxides and/or dental glasses, the total composition amounting to 100% by weight.

2. The composition according to claim 1, wherein the (a) at least one acrylic acid ester having an addition carboxy group, acrylic acid ester having at least one addition anhydride group of carboxy groups and/or the at least one derivative of the afore-mentioned acrylic acid esters is selected from an acrylic acid ester having an additional carboxy group of formula II or III

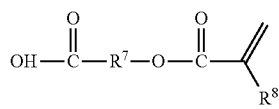

with $R^7$ each independently selected from bivalent C, H, O and optionally N containing groups having 1 to 25 C atoms, and $R^8$ is selected from H and 1 to 4 C alkyl,

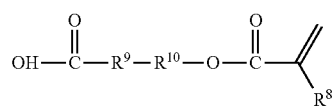

$R^9$ is independently selected from bivalent benzoyl, salicyloyl and derivatives thereof or -C-, $R^{10}$ is bivalent -$(OR^{11})_r$- with $R^{11}$ equal to ethylene or propylene and with r equal to 0 to 10, or $R^{10}$ is independently selected from bivalent alkylene and/or $R^8$ is selected from H and 1 to 4 C alkyl.

3. The composition according to claim 1, wherein
(a) the at least one acrylic acid ester having an additional carboxy group, acrylic acid ester having at least one addition anhydride group of carboxy groups and/or derivative of the afore-mentioned acrylic acid esters comprises 2-Acryloyloxyethyl hydrogen phthalate, polyether-functionalised acrylic acid esters having a carboxy group and/or 4-(2-methacryloxyethyl) trimellitic acid anhydride (4-META).

4. The composition according to claim 1, wherein the composition comprises at least one further monomer
(e.1) at least one mono-, tri-, tetra- or multi-functional monomer, not being a urethane (meth)acrylate, comprising (octahydro-4,7-metano-1H indenyl) methyl acrylate, and/or
(e.2) at least one at least di-functional urethane (meth)acrylate.

5. The composition according to claim 1, wherein
(b) the at least one di-functional acrylate having a bivalent alicyclic group and/or at least one di-functional methacrylate having a bivalent alicyclic group is selected from tricyclodecane dimethanol diacrylate (TCDDA), tricyclodecane dimethanol dimethacrylate, tricyclodecane diethanol diacrylate, tricyclodecane diethanol dimethacrylate, and/or mixtures thereof.

6. The composition according to claim 1, wherein
(c) the at least one disubstituted 4,4'-di(oxabenzene) dialkyl methane of formula I

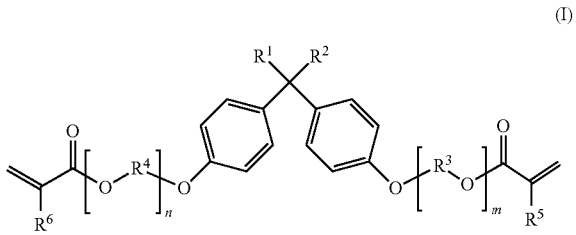

comprises $R^1$ and $R^2$ each methyl, and $R^5$ and $R^6$ the same and selected from H, methyl and ethyl, and with $R^3$ and $R^4$ each independently bivalent ethylene or propylene with n=2 to 4, and with m=2 to 4.

7. The composition according to claim 1, wherein the composition has a viscosity of less than 5000 m.Pas measured with a rheometer at 100/s 23 ° C.

8. The composition according to claim 1, wherein the primary particle sizes of the inorganic fillers, optionally being present as agglomerated and/or aggregated primary particles, have an average particle diameter of approximately 3 to 70 nm.

9. A polymerised composition according to claim 1, wherein the polymerised composition has alternatively or cumulatively a) a flexural strength of greater than or equal to 75 MPa according to DIN EN ISO 20795-2, and/or b) an E-modulus of greater than or equal to 2000 MPa according to DIN EN ISO 20795-2, and/or c) a bending fracture of greater than or equal to 1.7 MPa $m^{1/2}$ (DIN EN ISO 20795-2), and/or d) a fracture work of greater than 250 J/m² (DIN EN ISO 20795-2).

10. Blank in the form of a three-dimensional moulded body of a polymerised composition according to claim 1 for producing dental prosthetic parts, orthopaedic appliances or dental pre-forms, wherein the blank has a) a flexural strength of greater than or equal to 75 MPa according to DIN EN ISO 20795-2, and/or b) an E-modulus of greater than or equal to 2000 MPa according to DIN EN ISO 20795-2, and/or c) a bending fracture of greater than or equal to 1.7 Mpa $m^{1/2}$ (DIN EN ISO 20795-2), and/or d) a fracture work of greater than 250 J/m$^2$ (DIN EN ISO 20795-2).

11. A method of using a composition according to claim 1 for producing dental prosthetic parts, orthopaedic appliances or dental pre-forms in a rapid prototyping or in a rapid manufacturing or rapid tooling method.

12. The method according to claim 11, wherein the dental prosthetic parts comprise denture base or parts thereof, artificial teeth, dental arch having at least two to 16 artificial teeth being interdentally integrally connected, crowns, provisional crowns, total prostheses, total crowns, splints for orthodontic corrections (similar to Invisalign), dental bridges, abutments, suprastructures, dental bars, inlays, onlays, orthodontic appliances, such as occlusal splints, dental pre-forms of artificial teeth, surgical guides for implantology, mouthguards, and/or implants.

13. The composition according to claim 1, wherein the composition comprises
    (a) 30 to 55% by weight of at least one acrylic acid ester having an additional carboxy group, of an acrylic acid ester having at least one additional anhydride of carboxy groups and/or of derivatives of the afore-mentioned acrylic acid esters,
    (b) 10 to 25% by weight of at least one di-functional acrylate having a bivalent alicyclic group and/or of at least one di-functional methacrylate having a bivalent alicyclic group,
    (c) 20 to 50% by weight of at least one disubstituted 4,4' di(oxabenzene) dialkyl methane of formula I with R1, R2, R5 and R6 each independently selected from H or C1 to C4 alkyl, in particular R1 and R2 C1 to C4 alkyl, preferably methyl, and R5 and R6 the same and selected from H, methyl or ethyl, in particular R5 and R6 the same and selected from H or methyl, and with R3 and R4 each bivalent C1 to C4 alkylene, with n=2 to 4 and m=2 to 4,
    (d) 0.01 to 10% by weight photoinitiator for the UV and/or Vis spectral region,
    (e.1) 10 to 25% by weight of at least one mono-, tri-, tetra- or multi-functional monomer, not being a urethane (meth)acrylate, comprising (octahydro-4,7-metano-1H indenyl) methyl acrylate, and/or
    (f) optionally 0.01 to 7.5% by weight inorganic fillers comprising inorganic oxides or inorganic mixed oxides and/or dental glasses, in particular zirconium dioxide, mixed oxides of zirconium oxide and silicon dioxide, silicon dioxide, the total composition amounting to 100% by weight.

* * * * *